(12) United States Patent
Kantoff et al.

(10) Patent No.: US 6,300,060 B1
(45) Date of Patent: Oct. 9, 2001

(54) METHOD FOR PREDICTING THE RISK OF PROSTATE CANCER MORBIDITY AND MORTALITY

(75) Inventors: Philip W. Kantoff, Needham; Myles Brown, Newton; Edward Giovannucci, Wakefield, all of MA (US)

(73) Assignees: Dana-Farber Cancer Institute, Inc.; The Brigham and Women's Hospital, Inc., both of Boston, MA (US)

( * ) Notice: Subject to any disclaimer, the term of this patent is extended or adjusted under 35 U.S.C. 154(b) by 922 days.

(21) Appl. No.: 08/649,069

(22) Filed: May 16, 1996

Related U.S. Application Data

(63) Continuation-in-part of application No. 08/556,217, filed on Nov. 9, 1995, now abandoned.

(51) Int. Cl.$^7$ .............................. C12Q 1/68; C12P 19/34; C07H 21/02; C07H 21/04
(52) U.S. Cl. ........................ 435/6; 435/91.1; 435/91.2; 536/23.1; 536/24.31; 536/24.33
(58) Field of Search ................. 435/6, 183, 91.1, 435/91.2; 436/94; 536/23.5, 24.33, 24.31, 23.1; 935/76, 77

(56) References Cited

FOREIGN PATENT DOCUMENTS

WO95/31575    11/1995   (WO).

OTHER PUBLICATIONS

Terrell et al., "Microsatellite Instability in Adenocarcinoma of the Prostate," American Journal of Pathology, vol. 147, No. 3, pp. 799–805, Sep. 1995.*

Webster's II New Riverside University Dictionary, p. 239, 1994.*

Irvine, Ryan A. et al., "The CAG and GGC Microsatellites of the Androgen Receptor Gene Are in Linkage Disequilibrium in Men with Prostate Cancer," Cancer Research 55:1937–1940 (May 1, 1995).

Reichardt, Juergen K. et al., "Genetic Variability of the Human SRD5A2 Gene: Implications for Prostate Cancer," Cancer Research 55:3973–3975 (Sep. 15, 1995).

Davis, Daphne L. and Russell, David W., "Unusual length polymorphism in human steroid 5α–reductase type 2 gene (SRD5A2)," Human Molecular Genetics 2(6):820 (1993).

Schoenberg, Mark P. et al., "Microsatellite Mutation–($CAG_{24 \rightarrow 18}$) in the Androgen Receptor Gene in Human Prostate Cancer," Biochemical and Biophysical Research Communications, 198(1):74–80 (1994).

Chamberlain, Nancy L. et al., "The length and location of CAG trinucleotide repeats in the androgen receptor N-terminal domain affect transactivation function," Nucleic Acids Research 22(15):3181–3186 (1994).

Edwards, Al et al., "Genetic Variation at Five Trimeric and Tetrameric Tandem Repeat Lociin Four Human Population Groups," Genomics 12:241–253 (1992).

Coetzee, Gerhard A. and Ross, Ronald K., Prostate Cancer and the Androgen Receptor, Journal of the National Cancer Institute, 86(11):872–873 (1994).

Meloni, R. et al., "Trinucleotide repeat polymorphism at the human insulin–like growth factor I receptor gene (IGF1R)," Nucleic Acids Research, 20(6):1427.

Sleddens, H.F.B.M. et al., "Trinucleotide repeat polymorphism in the androgen receptor gene (AR)," Nucleic Acids Resarch, 20(6):1427.

\* cited by examiner

Primary Examiner—Bradley L. Sisson
(74) Attorney, Agent, or Firm—Hamilton, Brook, Smith & Reynolds, P.C.

(57) ABSTRACT

There is described a method for prognosis of prostate cancer in a male comprising: (a) determining the length of the CAG trinucleotide repeat of exon 1 of the androgenic receptor gene and/or the length of the TA dinucleotide repeat of the 5 alpha reductase Type II gene or its complement obtained from DNA of the male and (b) correlating the length of the repeat with the aggressiveness and mortality risk of the cancer in the male.

9 Claims, No Drawings

METHOD FOR PREDICTING THE RISK OF PROSTATE CANCER MORBIDITY AND MORTALITY

RELATED APPLICATIONS

This application is a Continuation-in-Part application of U.S. Ser. No. 08/556,217, filed Nov. 9, 1995, now abandoned, the entire teachings of which are incorporated herein.

BACKGROUND OF THE INVENTION

Prostate cancer is the most common malignant tumors and the second most common cause of cancer death in American males. Schoenberg, M. P., et al., Biochem. and Biophys. Res. Comm. 198: 74–80 (1994). Racial differences in the incidence of disease have also been observed, with the highest incidence in the African-American population, followed by Caucasians. The incidence of the disease is lowest in Asians. Interestingly, the androgen receptor gene contains a highly polymorphic CAG microsatellite in exon 1, resulting in a variable length glutamine repeat. The CAG repeat MEAN lengths observed in African-Americans, Caucasians and Asians are 18, 21 and 22, respectively. While the androgen receptor gene has been speculated to possess some relationship with prostate cancer, the nature of that relationship is unknown and the subject of speculation. Coetzee, G. A. and Ross, R. K., J. Natl. Cancer Inst. 86:872–73 (1994).

The human androgen receptor gene has been assigned chromosomal location Xq11–12 with the polymorphic CAG repeat region located at position 172 following the translation start codon. The polymorphism in the human androgen receptor gene has been used to diagnose families with the Androgen Insensitivity Syndromes, employing the polymerase chain reaction (PCR).

The relationship of the CAG repeat of the androgen receptor (AR) gene and prostate cancer has been studied. Schoenberg, M. P., and colleagues supra, describe a somatic contraction of the repeat region in one patient with prostate cancer, yet the PCR products of the tumor/non-tumor DNA in the remaining 39 patients studied were the same. No correlation of the CAG repeat length to the aggressiveness or mortality of prostate cancer has been suggested.

SUMMARY OF THE INVENTION

The present invention is based upon the discovery that the number of CAG repeats in the androgen receptor determines the aggressiveness of prostate cancer and the likelihood that a patient of at least about 60 years of age will die of the disease. For total prostate cancer, a slight inverse association between androgen receptor CAG repeat length and risk of disease was observed, but this was not statistically significant. However, CAG repeat length was inversely associated with cancers characterized as "aggressive" (extraprostatic extension (stage C or D) and/or high grade). For an increment of six CAG repeats, equivalent to the difference between the median CAG length in the upper versus lower tertile of CAG repeats, the relative risk of "aggressive" prostate cancer was 0.66 (95 percent confidence interval, 0.44–0.96; p=0.03) and the relative risk for developing distant metastatic prostate cancer was 0.41 (95 percent confidence interval, 0.21–0.81; p=0.01). CAG repeat length was not associated with non-aggressive disease. Results presented herein demonstrate an inverse correlation between CAG repeat length and indicators of disease progression (p, trend,=0.005). Risk of advanced, aggressive, or fatal disease was particularly strongly related to CAG length among older men.

The results herein also provide evidence that the variability in the androgen receptor CAG microsatellite influences the risk of developing "aggressive" prostate cancer. As a result, a method of predicting the onset of aggressive prostate cancer and the risk of mortality from the prostate cancer is available.

The present invention additionally relates to the discovery that the length of the TA repeat polymorphism in the 5-alpha reductase gene is directly related with risk of aggressive disease. Thus, the invention relates to a method for prognosis of prostate cancer in a male comprising: (a) determining the length of the TA dinucleotide repeat in the 5-alpha reductase gene and (b) correlating the length of the repeat with the risk of prostate cancer in the male.

DETAILED DESCRIPTION OF THE INVENTION

Cell division in the prostate gland is controlled by testosterone (Coffey D. S., UICC Technical Report Series, 48:4–23, Geneva: International Union Against Cancer, (1979)). In the prostate cell, testosterone is converted to dihydrotestosterone (DHT) through the action of 5-alpha-reductase (Thigpen, A. E., et al., N.E. J. Med., 327:1216–19 (1992)). DHT binds with the androgen receptor (AR) in the cell nucleus, and the DHT-AR complex interacts with specific DNA sequences, resulting in up- or down-regulation of target genes. Encoded in exon 1 of the AR gene on the X-chromosome are polymorphic CAG microsatellites. The CAG repeats, which range normally from about 8 to 31 repeats and average about 20, (Edwards A., et al. Genomics 12:241–53 (1992)) encode for polyglutamine chains in the transactivation region of the AR. In transfection assays, the lengths of these polyglutamine chains correlate inversely with transactivation of the AR (Chamberlain, N. L., et al., Nucleic Acids Res., 22:3181l4 6 (1994); Kazemi-Esfarjani P., et al., Human Molecular Genetics, 4:523–7 (1995)). Expansion of the CAG microsatellite to 40 to 62 repeats, which causes X-linked spinal and bulbar muscular atrophy (Kennedy's disease), leads to signs of relative androgen insensitivity, including hypogonadism, reduced fertility with oligospermia or azoospermia, and gynecomastia despite normal serum testosterone levels in men (LaSpada, A. R., et al., Nature, 352:77–9 (1991); Arbizu, T., et al., J. Neurol. Sci., 59:371–82 (1983); Igarashi, S., et al., Neurology, 42:2300–2 (1992)).

Because of their role in prostate cell division, androgens are believed to influence the initiation or promotion of prostate Cancer (Ross, R. K., et al., cancer, 75:1778–1782 (1995)). Moreover, the variation in androgen receptor transactivation related to polymorphism in CAG repeat length could influence occurrence or progression of prostate cancer. Coetzee and Ross have hypothesized that the generally shorter CAG repeat lengths in the AR among African-Americans may contribute to their high incidence of prostate cancer, particularly advanced cancer (Coetzee, G. A., Ross, R. K., J. Natl. Cancer Inst., 86:872–3 (1994)). A slight inverse association between CAG repeat length and risk of prostate cancer has been reported, but this finding was based on only 47 cases and was not statistically significant (Irvine, R. A., et al., Cancer Res., 55:1937–40 (1995)). Hence, the relationship between polymorphism in CAG repeat length in the AR and prostate cancer development and progression in a large cohort study was examined, the Physician's Health Study.

As set forth above, the invention relates to a method for prognosis of prostate cancer in a male comprising: (a)

determining the length of the CAG trinucleotide repeat of exon 1 of the androgenic receptor gene and/or the length of the TA dinucleotide repeat in the 5-alpha reductase gene obtained from DNA of the male and (b) correlating the length of the repeat with the aggressiveness and mortality risk of the cancer in the male.

The invention also relates to a method for determining length of a CAG trinucleotide repeat in exon 1 of the androgenic receptor gene and/or the length of the TA dinucleotide repeat in the 5-alpha reductase gene or its complement in a male patient having prostate cancer comprising: (a) obtaining DNA from the patient wherein the DNA comprises the CAG trinucleotide repeat of exon 1 of the androgenic receptor gene and/or the length of the TA dinucleotide repeat in the 5-alpha reductase gene or its complement; (b) determining the length of the repeat; and (c) comparing the length of the repeat with the length of the repeat in a significant number of individuals; wherein the length of the repeat is prognostic of the aggressiveness and mortality of the prostate cancer.

As detailed above, the length of the AR CAG repeat in the germline is inversely related to the onset of aggressive prostate cancer and mortality due to prostate cancer, particularly in males over about 60 years of age. The male to be tested can be of any race, including African-American, Caucasian or Asian. A suitable controllor comparison can be obtained for example, from males, including males of all races. Accuracy of the method can be increased by comparing the length of the CAG repeat in the male patient with the mean or average values of the length of the CAG repeat in males of the same race. That is, an appropriate control for comparing the length of the repeat as a prognostic can include the mean and/or average length of the repeat in a population of males of the same racial background or origin. Of course, random selection of a significant number of males improves the statistical significance of the control population.

Another embodiment of the invention includes screening for a TA repeat polymorphism in the 5 alpha reductase gene. The development and progression of prostate cancer (CaP) is believed to be influenced by androgen hormones. The 5 alpha reductase, Type II, converts testosterone to dihydrotestosterone and is critical to the development of the prostate. A TA dinucleotide repeat polymorphism exists in the 3' untranslated region of the 5 alpha reductase, Type II, gene. The 5 alpha reductase alleles with longer TA repeats are more common in African-Americans, the group with the highest incidence of CaP. While investigators speculated that the length of the TA repeat region of the 5 alpha reductase gene in the germline of males was inversely related to the later incidence of prostate cancer or its morbidity, the results reported below support the opposite conclusion.

The 5 alpha reductase converts testosterone to dihydrotestosterone (DHT), the most potent natural ligand of the androgen receptor. Two isozymes of 5 alpha reductase exist (Jenkins, E. P., et al., *J. Clin. Invest.*, 89:293–300 (1992)). The 5 alpha reductase, Type I, has its gene on chromosome 5 and codes for a protein which is expressed in the liver, skin, and scalp (Jenkins-, E. P., et al., *Genomics*, 11:1102–1112 (1991); Thigpen, A. E., et al.,*J. Clin. Invest.*, 92:903–910 (1993)). There is no known phenotype for mutations of this first isozyme (Thigpen, A. E., et al.,*J. Clin. Invest.*, 92:903–910 (1993)). The 5 alpha reductase, Type II (SAR5A2) has its gene on chromosome 2 and is required for the development of the male external genitalia and growth of the prostate (Wilson, J. D., *Ann. Rev. Phys.*, 40:279–306 (1978)). Deficiency of 5 alpha reductase, Type II, activity leads to a phenotype known as pseudohermaphroditism (Thigpen, A. E., et al.,*J. Clin. Invest.*, 90:799–809 (1992)). Affected boys have ambiguous external genitalia and a rudimentary prostate (Wilson, J. D., *Ann. Rev. Phys.*, 40:279–306 (1978); Anderson, S., et al., *Nature*, 354:159–161 (1991)). In older men, 5 alpha reductase activity is present in the stroma of normal prostate and increased in stroma associated with benign prostatic hypertrophy (Silver, R. I., et al., *J. of Urology*, 152:433–437 (1994)).

Because of its role in prostate ontogeny and growth, alterations in the function of 5 alpha reductase, Type II, could potentially affect an individual's risk of CaP. Even small alterations in the function of 5 alpha reductase could, over a lifetime, decrease levels of intraprostatic DHT significantly enough to alter the incidence of prostate cancer.

Different levels of androgen hormones have been suggested as one possible explanation of the observed difference in rates of CaP between ethnic groups. Ross and colleagues measured surrogate markers of 5 alpha reductase activity in young Japanese, African-American, and Caucasian men. They found Japanese men, who have the lowest rates of CaP, to have hormone levels consistent with lower 5 alpha reductase activity than African-American and Caucasian men (whose hormone levels were not significantly different from one another) (Ross, R. K., et al., *The Lancet*, 339:887–889 (1992)). This indirectly suggested that the activity of this enzyme may play a role in the low rates of CaP observed in Japanese men.

SRD5A2 has a polymorphism in its 3' untranslated region. Russell et al. demonstrated three alleles which differ in the number of TA dinucleotide repeats, TA(0), TA(9), and TA(18) (Davis, D. L. and Russell, D. W., *Human Molec. Genetics*, 2:820 (1993)). Although there is some minor variation in the exact number of TA repeats, the labels adequately describe the three clusters of families observed (Ross, R. K., and colleagues, *Cancer*, 75:1778–1782 (1995)). Recently, Reichardt et al. confirmed that the TA(0) allele family is most common and the TA(18) allele family is found almost exclusively in African-American men (Reichardt, J. K. V., et al., *Cancer Res.*, 55:3973–3975 (1995)). The hypothesis has been set forth that these longer alleles may be associated with an increased risk of CaP and may partially explain the observed racial differences in CaP.

To study the three allele families and their association with CaP a case control study was performed of 368 prevalent cases of men with prostate cancer and 368 matched controls all participants in the Physicians Health Study. The polymorphic nature of this gene and the relative allele frequencies reported by Reichardt et al. was confirmed as described below. A statistically significant, decreased risk of prostate cancer among patients homozygous for the longer TA allele families, a truly surprising result, was also demonstrated.

Either DNA or RNA can be used in the present method. The DNA which can be used in the method can be cDNA or genomic DNA, preferably genomic DNA. The source of DNA can be from any cell or cells removed from the individual and can include cultured progeny thereof. Since the invention does not rely upon the identification of somatic mutation in the tumor, but is preferably analyzing germline DNA, the DNA can be isolated from non-cancerous cells, such as somatic tissue or a blood sample. Also because the DNA which is preferably analyzed is germline DNA, the prognostic method can be carried out prior to onset of disease. This significant advantage can be used to establish a cancer screening schedule prior to onset of prostate cancer and treatment protocol upon onset due to the risk factor assigned by the described method.

The AR CAG repeat length or 5-alpha reductase TA repeat length can be determined using methods generally known in the art, such as by PCR (described herein below). Alternatively, the DNA comprising the repeat or its complement can be sequenced, thereby identifying the repeat length. In yet another embodiment, the protein encoded by the DNA can be sequenced or identified, thereby establishing the length of the repeat. Since CAG encodes the amino acid glutamine, the identification of the number of glutamine residues in the corresponding region of the androgen receptor protein directly indicates the number of CAG repeats. In yet another embodiment, an antibody which binds a polyglutamine residue selectively by length can be made and used to screen a protein fraction which contains the androgen receptor.

The number of CAG repeats in the AR gene or the number of TA repeats in the 5-alpha reductase gene can be determined by methods known in the art. The source of DNA, cDNA or RNA can be from patient biological samples, such as blood, biopsy tissue, sperm, fibroblasts or other somatic or germline cells.

One such method is PCR methods using a pair of primers specific for sequence flanking the CAG repeat region of exon 1 or the TA repeat region in the 5 alpha reductase gene. The resulting products can be sequenced, analyzed for size on gels, such as polyacrylamide or agarose gels, or evaluated by physical characteristics such as melting temperature or secondary structure. Other methods for determining size of nucleic acid fragments can be employed.

Co-amplification of two alleles in a heterozygote can generate PCR products which differ in the number of repeats and therefore their melting and secondary structure characteristics are likely to differ. Under conditions as described in, e.g., Mutter, G. L., and Boynton, K. A., (Nucleic Acids Res., 23:1411–18 (1995), amplification efficiency of the two alleles is near-equivalent, generating PCR products in a ratio proportional to that of the genomic template. Variability and biasing can be diminished by substitution of 7-deaza-2'-dGTP for dGTP during amplification, an intervention which reduces stability of intramolecular and intermolecular GC basepairing.

Allelic PCR fragments are easily separated, for example, by gel electrophoresis and detected by intercalating dye staining (e.g., ethidium bromide). As an alternative procedure, capillary electrophoresis can be employed. One example of capillary electrophoresis is in a polymer network consisting of 8% polyacryloylaminoethoxyethanol in the absence of cross-linker, and offers a simple procedure for separation and on-line detection via UV absorbance at 254 nm, thus avoiding additional staining steps. The capillary column can be used repeatedly and the electropherogram can be stored on magnetic support. Comparisons among different runs can be obtained aligning all tracings to an internal standard of a known base pair size added as a marker (Nesi, M. et al., Electrophoresis, 15:644–6 (1994)).

In yet another embodiment, the number of repeats can be determined according to the method of Yamamoto and colleagues (Biochem. Biophys. Res. Comm. 182:507–13 (1992)). The DNA obtained from the male containing the repeat is amplified by standard PCR, a primer extension is carried out following addition of dideoxy ATP to the reaction mixture. The extension of the end-labeled reverse primer adjacent to 3' end of the repeats stops at the first T after the repeats and the resultant primer products can be analyzed by denaturing polyacrylamide gel electrophoresis and autoradiography.

Additional PCR based methods which can be used include random rapid amplification of cDNA ends (RACE), described by Carney and colleagues (Gene, 155:289, 1995); single strand conformation polymorphism analysis (Ris-Stalpers C., et al., Pediatric Res., 36:227–34 (1994)) and reverse transcriptase PCR (Nakamura, M., et al., J. Neurological Sci. 122:74 (1994)). Additional hybridization techniques include the use of probes of varying CAG repeat lengths labeled with the same or different radioactive or fluorescent dyes, for example. This method allows for the direct detection of CAG repeats (see, e.g., Sanpei, K., et al., Biochem. Biophys. Res. Comm. 212:341–6 (1995); Taneja, K. L., J. Cell Biol. 128:995–1002 (1995) and Saito, F., Jpn. J. of Human Genet., 39:421–5 (1994)).

In yet another embodiment the protein which is encoded by a repeat-containing fragment or the gene, or in the alternative, the nucleic acid, can be separated by size using art-recognized separation media and methods. Standard polyacrylamide gels or a modified SDS-PAGE protocol using low concentration of methylenebisacrylamide and long runs (Ide, K., et al., Biochem. Biophys. Res. Comm. 209:1119–25 (1995)).

Alternatively, reverse blot techniques can be employed for determining a small number of repeats or differences in repeats as described by Wehnert and colleagues (Nucleic Acids Res. 22:1701–4 (1994)). In this method, oligonucleotides representing trinucleotides (21mers) tandem repeats are directly synthesized and arrayed onto an aminated substrate (e.g., polypropylene). DNA samples of different complexities can be used and are radiolabelled and hybridized to the oligonucleotide array. The reverse blot system specifically identifies trinucleotide short random repeats (STRs). There is low to no random or crosshybridization to nonspecific sequences and it is possible to detect as few as three repeated units in a particular location. Varying the hybridization stringency can enhance the detection of STRs. This single step reverse blot system therefore allows the rapid, specific and sensitive identification of various STRs in DNA sources of different complexity.

In yet another embodiment, CAG binding proteins, TRIP-1 and TRIP-2, as described by Yano-Yanagisawa and colleagues (Nucleic Acids Res. 23:2654–60 (1995)) can be used to isolate CAG-containing DNA. These proteins may also require a minimum of eight (AGC) trinucleotide repeating units for recognition and binding.

The term "prognosis" is defined herein as the judgement in advance concerning the probable course of a disease and/or the chances of recovery.

The invention can be utilized particularly advantageously in combination with the information made available in other screening assays and risk factor assessment methods and criteria.

The present invention will now be illustrated by the following examples, which are not intended to be limiting in any way.

EXEMPLIFICATION

EXAMPLE 1

Methods

Study Population

The Physician's Health Study is an ongoing randomized double-blind, placebo-controlled trial of beta-carotene among 22,071 U.S. male physicians, aged 40 to 84 years in 1982. The cohort is predominantly white (over 95%). Men were excluded if they reported a prior history of myocardial infarction, stroke, transient ischemic attacks, unstable angina, cancer (except for non-melanoma skin cancer), current renal or liver disease, peptic ulcer or gout, contraindication to use of aspirin, or current use of aspirin, other platelet-active agents or vitamin A supplements. The trial had included an aspirin component that was terminated in January, 1988 due primarily to a 44% reduction in the risk of a first myocardial infarction among those in the aspirin group (Steering Committee of the Physicians' Health Study Res. Group, *N.E. J. Med.*, 321:129–35 (1989)).

Study participants completed two mailed questionnaires before randomization in 1982, and additional questionnaires at six months, 12 months, and annually thereafter. Before randomization blood kits were sent to all participants with instructions to have their blood drawn into vacutainer tubes containing EDTA, to centrifuge them, and to return the plasma in polypropylene cryopreservation vials. The kit included a cold pack to keep the specimens cool until receipt the following morning, when they were aliquoted and stored at −82° C. During storage, precautions were taken so that no specimen thawed or warmed substantially. Specimens were received from 14,916 (68%) of the randomized physicians; over 70% between September and November, 1982.

Selection of Cases and Controls

When a participant reported a diagnosis of cancer on the follow-up questionnaires, medical records, including pathology reports, that were reviewed by study physicians from the End Points Committee were requested. By March, 1992, 520 cases of prostate cancer, of which 368 had provided blood, were confirmed. The lack of blood samples for some study participants is unlikely to have introduced selection bias, since it is unlikely that physicians who did or did not provide a sample would differ in terms of the relationship of the AR CAG microsatellite to subsequent prostate cancer experience. For each case, one control who had provided plasma, had not had a previous prostatectomy, and had not reported a diagnosis of prostate cancer at the time diagnosis was reported by the case, was selected. Controls were also matched on smoking status and age within one year, except for several very elderly cases for whom age had to be matched within two years. After 10 years of follow-up, over 99% of the men were still reporting morbidity events, and vital status was ascertained for 100%.

Medical Record Review

A study physician, unaware of assay results, reviewed medical records for each case to determine stage at diagnosis, tumor grade, Gleason score, type of presentation (e.g., symptoms, screening rectal exam, etc.), and treatment modalities. Stage was recorded according to the modified Whitmore-Jewett classification scheme (Beahrs O. H., et al., *Manual for staging of cancer. 4th ed.* Philadelphia: J. B. Lippincott (1992)). If multiple tissue samples were examined, the highest reported grade and Gleason score were recorded. Cases without pathological staging were classified as indeterminate stage unless there was clinical evidence of distant metastases. "Aggressive" cases were defined as those diagnosed at stage C or D (extraprostatic) plus those diagnosed at stage A or B or indeterminate with either poor histologic differentiation or Gleason score 7 or greater. Cases with clinical stage A or B or no pathological staging, and moderate or better histologic grade were classified as non-aggressive. Among patients with localized prostate cancers, those with poor histological features have increased mortality, and thus warrant categorization as aggressive (Gleason, D. F., et al., *J. Urology*, 111:58–64 (1974)). In this cohort, 69% of the fatal cases occurred in men (27.8% of total) designated with both advanced stage (at diagnosis) and histologically aggressive tumors. By 1992, 27.5% of men with tumors both high grade and stage had died of prostate cancer, whereas only 4.3% of all others had died by the end of follow-up.

Analysis for CAG Repeat Length in the Androgen Receptor

Since the AR gene is X-linked, only one copy of the gene exists in men. The CAG microsatellite region resides in the coding region of the gene within the first exon. A system to rapidly analyze the CAG repeat sequence length in a large number of samples was established. Five hundred microliters of whole blood was thawed from cases and controls and DNA was extracted utilizing the Qiagen QIAamp Blood Kit. A set of oligonucleotide primers that span the CAG repeat (5'TCCAGAATCTGTTCCAGAGCGTGC3' (SEQ ID NO:1) and 5'GCTGTGAAGGTTGCTGTTCCTCAT3' (SEQ ID NO:2)) were constructed. The DNA was amplified using these primers by polymerase chain reaction (PCR) to produce fragments of the N-terminal domain of the AR. The length of these fragments varied only by the number of CAG repeats. For rapid and accurate assessment of fragment length, the DNA fragments were run on a 6% denaturing polyacrylamide gel by automated fluorescence detection (Genescan Applied Biosystems). Using a series of sequenced PCR products of varying size, DNA markers were used to create a standard curve of peak arrival time that in turn was used to calculate the length of an unknown PCR product automatically. Resolution of 1 base pair using this system was confirmed with direct DNA sequencing. The assays were conducted by laboratory personnel blinded to case-control status. Split samples were used to ensure quality control. It was possible to amplify 367 of the 368 cases.

Data Analysis

Analyses to determine whether AR CAG repeat length was related to total prostate cancer and, secondly, to malignancies of increased aggressiveness were conducted. Aggressive behavior was determined by combinations of 3 sets of data, histology (tumor grade or Gleason score), tumor stage, and fatality. The relative risk (estimated by the odds ratio) of developing total, aggressive, non-aggressive, high-grade, advanced-stage, and fatal prostate cancer was examined. Unconditional logistic regression, controlling for age and smoking, the matching variables, to compute odds ratios and 95 percent confidence intervals, after first conducting conditional logistic regression to confirm similar results was used. By using unconditional logistic regression, information from all controls in the analyses limited to a subset of cases (e.g. aggressive or fatal cases) could be utilized. Analyses limited to cases to examine various parameters of aggressive behavior (stage, grade, fatality) in relation to CAG repeat length were also conducted.

CAG repeat lengths as a continuous variable in logistic models were analyzed, which maximizes efficiency under the assumption that a one unit increment in CAG repeat length is related to a constant increase or decrease in the natural logarithm of the odds ratio. The p-value for the continuous variable formed the basis of the test for trend.

Men were categorized into groups to observe if non-monotonic increases existed across levels of CAG repeats are results for high grade and advanced stage lesions separately.

TABLE 1

| | CAG Length | | | | | | P-value |
|---|---|---|---|---|---|---|---|
| | ≦19 | 20 | 21 | 22–23 | 24–25 | ≧26 | (Trend) |
| Controls | 76 | 44 | 60 | 61 | 86 | 40 | |
| Total Prostate Cancer (n) | 79 | 45 | 70 | 71 | 64 | 38 | |
| OR | 1.0 | 0.97 | 1.11 | 1.11 | 0.71 | 0.91 | 0.21 |
| 95% CI | — | (0.57–1.65) | (0.70–1.79) | (0.70–1.78) | (0.45–1.12) | (0.53–1.58) | |
| Aggressive Prostate Cancer (n) | 35 | 28 | 33 | 54 | 24 | 18 | |
| OR | 1.0 | 1.07 | 0.96 | 0.96 | 0.48 | 0.78 | 0.03 |
| 95% CI | — | (0.58–1.97) | (0.54–1.70) | (0.55–1.69) | (0.27–0.87) | (0.40–1.55) | |
| Non-Aggressive Prostate Cancer (n) | 34 | 17 | 37 | 54 | 40 | 20 | |
| OR | 1.0 | 0.85 | 1.39 | 1.36 | 1.00 | 1.07 | 0.98 |
| 95% CI | — | (0.42–1.71) | (0.77–2.50) | (0.76–2.44) | (0.57–1.75) | (0.54–2.11) | |
| Fatal Prostate Cancer (n) | 12 | 5 | 7 | 3 | 7 | 2 | |
| OR | 1.0 | 0.73 | 0.64 | 0.31 | 0.49 | 0.30 | 0.06 |
| 95% CI | — | (0.24–2.25) | (0.23–1.78) | (0.08–1.16) | (0.18–1.35) | (0.06–1.45) | |

(e.g., if a threshold existed). The categorization (ranging from ≦19 to ≧26 repeats) was based on approximating a relatively equal distribution of the values, although the numbers in the categories fluctuated somewhat because of the very uneven distribution. All decisions for categorization were conducted before the analyses were conducted. Potential confounding by alcohol consumption, multivitamin use, body mass index and exercise level on the 1982 questionnaire, and aspirin use based on randomization, was addressed by including these as covariates in multivariate models. All reported p-values are based on two-sided tests.

Results

The range in CAG repeats in the AR ranged from 14 to 32 among cases and from 8 to 39 among controls. The mean (and standard deviation) for CAG repeats was 21.87 (3.07) for cases and 21.95 (3.46) for controls. The difference in means was not statistically significant. As had been seen in other Caucasian populations, a bimodal distribution was observed with a primary peak at 21 CAG repeats and a secondary peak at 24 to 25 CAG repeats (Edwards A., et al. Genomics 12:241–53 (1992)).

Next the relative risks (odds ratios, OR) for total and sub-groups of prostate cancers by CAG repeat length were examined. For total prostate cancer, a slight inverse association between CAG repeat size and risk of disease was observed, but this was not statistically significant. However, statistically significant inverse associations for cancers characterized by various indicators of aggressive or advanced disease was noted, whereas no association was noted for non-aggressive cases. Only 36 of the cases of prostate cancers were fatal in this time period, but a strong inverse association between CAG repeat length and fatal prostate cancer was observed, although this just missed attaining conventional statistical significance. AR CAG length was not correlated with any cofactor considered (age, year of diagnosis, alcohol intake, physical activity, multivitamin use, body mass index, and aspirin use); hence, the results were unaltered when these were included as covariates in models. Also, Table 1 reports odds ratio for a six-CAG increment (equivalent to the difference between the median CAG repeat between the high and low tertiles). Also shown The relationship between CAG repeat length and risk of prostate cancer by age group was examined. No appreciable association in men younger than about 60 years, but progressively stronger inverse associations for men 60 to 69 years and men 70 years or older for prostate cancer (Table 2) were found. A statistically significant multiplicative interaction (P=0.015) existed between age of disease and CAG length for total prostate cancer, as well as for most of the sub-groups of cases. In essence, among the men over the age of 60 years, the CAG repeat length was an important predictor of risk, whereas among those under 60 years, CAG repeat length was weakly or unrelated to risk. Risk of advanced, aggressive, or fatal disease was particularly strongly related to CAG length among the older men.

TABLE 2

| | Total | Men <65 yrs old | Men ≧65 yrs old |
|---|---|---|---|
| Total Prostate Cancer Cases (n) | 367 | 199 | 168 |
| OR (95% CI) | 0.75 (0.48–1.17) | 1.05 (0.56–1.95) | 0.52 (0.27–1.01) |
| Non-Aggressive Prostate Cancer Cases (n) | 185 | 90 | 95 |
| OR (95% CI) | 1.01 (0.58–1.74) | 1.40 (0.63–3.11) | 0.75 (0.35–1.61) |
| Aggressive Prostate Cancer Cases (n) | 182 | 109 | 73 |
| OR (95% CI) | 0.54 (0.31–0.95) | 0.82 (0.39–1.73) | 0.30 (0.12–0.73) |
| High Grade Prostate Cancer Cases (n) | 134 | 83 | 51 |
| OR (95% CI) | 0.54 (0.29–1.02) | 0.85 (0.37–1.95) | 0.29 (0.10–0.79) |
| Advanced Stage Prostate Cancer Cases (n) | 140 | 84 | 56 |

TABLE 2-continued

|  | Total | Men <65 yrs old | Men ≧65 yrs old |
|---|---|---|---|
| OR (95% CI) | 0.52 (0.28–0.98) | 0.92 (0.40–2.08) | 0.25 (0.09–0.68) |
| Fatal Prostate Cancer Cases (n) | 36 | 17 | 19 |
| OR (95% CI) | 0.33 (0.11–1.04) | 1.18 (0.23–6.10) | 0.09 (0.01–0.54) |

The mean CAG repeat length among the different classes of tumors was examined. Men with non-aggressive tumors had a slightly higher CAG repeat length than controls, but this was not statistically significant. Aggressive cases, defined by both grade and stage, had lower mean CAG repeat lengths. These differences were statistically significant for advanced cases (P=0.02) and high grade cases (P=0.03), or either (P=0.01), for distant metastatic or fatal cases (P=0.008). The difference in fatal cases was less striking (P=0.06). A test for trend in CAG repeat length across 3 levels of disease (non-aggressive disease, aggressive but regional disease, and distant disease) using progressive ordinal values was highly significant (P=0.005) in a linear regression model (Table 3).

TABLE 3

|  | n | Means (SD) | P-Value |
|---|---|---|---|
| Controls | 367 | 21.95 (3.46) | — |
| stage A or B and Gleason ≦ 6 | 185 | 22.26 (3.14) | — |
| Stage C or D or Gleason ≧ 7 | 182 | 21.47 (2.95) | 0.01 |
| Stage C or D | 139 | 21.47 (2.88) | 0.02 |
| Gleason ≧ 7 | 134 | 21.49 (3.00) | 0.03 |
| Fatal Cases | 36 | 21.17 (2.94) | 0.06 |

Discussion

A low number of CAG repeats in exon 1 of the AR gene was closely related to aggressive behavior in prostate cancer, as defined by various measures including histological grade, stage at diagnosis, and mortality. Results were consistent whether men with aggressive lesions to prostate cancer-free controls or to men with non-aggressive prostate cancer were compared, and CAG repeat length tended to decrease as the indicator of aggressiveness progressed, as from regionally aggressive to distant disease. The reliance on pathology reports to document Gleason score and tumor grade probably results in some degree of measurement error, but this impression would tend to attenuate any true associations. Nonetheless, these histological parameters were strong predictors of mortality from the disease, which supports the quality of the reports.

Prostatic cancer appears to depend on the presence of androgens (Coffey D. S., *UICC Technical Report Series*, 48:4–23, Geneva: International Union Against Cancer, (1979)). Early prostate cancer is sensitive to androgens and often regresses when androgen stimulation is withdrawn (Coffey D. S., *UICC Technical Report Series*, 48:4–23, Geneva: International Union Against Cancer, (1979)). Prostate cancer occurs rarely in castrated men (Hovenian, M. S. and Deming, C. L., *Surg. Gynecol. Obstet.*, 86:29–35 (1948)), and the prolonged administration of high levels of testosterone has induced prostate cancer in rats (Noble, R. L., *Cancer Res.*, 37:1929–1933 (1977); Pollard, M., et al., *Prostate*, 4:563–568 (1982)). Patients with cirrhosis, characterized by high estrogen and low testosterone levels, appear to also be at lower risk of prostate cancer (Robsin, M. C., *Geriatrics*, 21:150–154 (1966)). However, whether hormone levels within normal ranges are important determinants of prostate cancer remains unsubstantiated (Zaridze, D. G. and Boyle, P., *British J. of Urology*, 59:493–502 (1987); Nomura, A., et al., Cancer Res., 48:3515–3517 (1988); Hsing, A. W. and Comstock, G. W., *Cancer Epidemiology Biomarkers & Prevention*, 2:27–32 (1993); Barrett-Connor, E., et al., *Cancer Res.*, 50:169–173 (1990)). The action of androgens is ultimately mediated through the androgen receptor. In transfection experiments, polyglutamine tract length in the AR is associated with lower transactivation. This inverse association is length-dependent, and occurs even within the normal range of CAG repeats (Chamberlain, N. L., et al., *Nucleic Acids Res.*, 22:3181–6 (1994)). DNA and androgen binding, which occur in different regions of the AR, appear to be unaffected by CAG length. Abnormally high CAG repeat length ($\geq 40$), which causes spinobulbar muscular atrophy or Kennedy syndrome, is associated with clinical androgen insensitivity in men (LaSpada, A. R., et al., *Nature*, 352:77–9 (1991); Igarashi, S., et al., *Neurology*, 42:2300–2 (1992)). Limited but inconclusive evidence suggests that polyglutamine length of the AR within the normal range (e.g. 12–27) correlate with androgenic characteristics (Legro, R. S., et al., *Obstet. Gynecol.*, 83:701–706 (1994)). Given clear evidence of clinical androgen insensitivity with long CAG repeat lengths and the linear gradient between CAG repeat length and AR transactivation in vitro, it is reasonable to assume that variation within the normal range is associated with physiologic effects, albeit subtle, in cells.

The results suggest that polymorphisms in the CAG repeat lengths of the AR, which are correlated with AR transactivity, influence the promotion or progression of prostatic tumors. Of note, a somatic mutation which resulted in a contraction of the CAG microsatellite ($CAG_{24 \rightarrow 18}$) was observed in an adenocarcinoma of the prostate (Schoenberg, M. P., et al., *Biochem. Biophys. Res. Comm.*, 198:74–80 (1994)), although whether this contraction was directly involved in the development or progression of the tumor is unknown.

While the inverse association with aggressive cancers was statistically significant in the entire population, the magnitude of the association escalated sharply with increasing age, a surprising result. At least two factors may account for the apparently stronger relationship among older men. Among younger men, a substantial proportion of prostate cancers is probably related to a rare, autosomal dominant, highly penetrant allele (Carter, B. S., et al., *Proc. Natl. Acad. Sci., USA*, 89:3367–3371 (1992)). Of the cumulative total of prostate cancers occurring by ages 55, 70, and 85 years, this allele appeared to be responsible for 43%, 34%, and 9%, respectively, of the total cases occurring by these ages. Given that almost 40% of the cancers among men younger than the age of 60 years is determined largely by the highly penetrant germline mutation, the relative contribution of the AR polymorphism may be substantially attenuated.

Another potentially relevant factor may be the hormonal changes related to aging, particularly the major reduction in free testosterone and an increase in estrogen levels (Sandberg, A. A., *The Prostate*, 1:169–184 (1980)). The overall reduction in androgenicity related to aging parallels the decreasing proportion of advanced stage and high grade tumors (32.2% among men under 60 years, 27.5% among men 60 to 69 years, and 21.5% among men 70 years or older in our data). Possibly, that AR CAG repeat length is a more important determinant of transactivation in a low androgen environment. A substantially larger study population than the current one would be required for sufficient power to examine the interaction between AR CAG repeat length and hormone levels.

It is worth noting that, due to the low numbers of older men in the Physician's Health Study, 33% of the cancers were diagnosed in men younger than age 60 years. In contrast, almost 90% of prostate malignancies occur among men over the age of 60 years in the general U.S. population. Thus, the numerical impact of this polymorphism in the general U.S. population may be even greater than our overall findings would suggest.

Even when African-American or black men have equal access to health care as whites in the U.S., the black men have about a two-fold higher rate of metastatic prostate disease and mortality, larger tumor volumes, and higher PSA values (Brawn, P. N., et al., *Cancer*, 71:2569–2573 (1993); Moul, J. W., et al., *JAMA*, 274:1277–1281 (1995)). Although the equal access to care does not assure equal utilization, these data are strongly indicative of a more aggressive tumor biology among blacks. Based on the different distributions of AR CAG repeats among black and white men in the U.S. (Edwards A., et al. *Genomics* 12:241–53 (1992)), and on our estimated relative risk of fatal prostate cancer related to CAG repeat length, we calculated a 54% greater risk of dying from prostate cancer among blacks 60 years and older than whites. U.S. black men also have higher levels of bioavailable testosterone than whites (Ross, R. K., et al., *J. Natl., Cancer Inst.*, 76:45–48 (1986)) and appear exposed to higher levels of estrogen and testosterone in utero (Henderson, B. E., et al., *Br. J. Cancer*, 57:216–218 (1988)). Although the relationship between CAG repeat length and prostate cancer risk should be confirmed directly in black men, our study design (largely restricted to a single racial group) provides strong evidence of causality. In fact, an association between CAG length and prostate cancer risk observed in a racially heterogenous population is likely to be confounded by any factor (genetic or environmental) that varies across the racial groups.

This polymorphism in the androgen receptor is interesting in another respect. Most known germline mutations that confer higher risk of cancer (e.g. BRCA1 in breast, mismatch repair genes in colon, putative prostate cancer suppressor gene) are characterized by early age of disease onset, high population attributable risk at young ages, but a relatively low attributable risk due to the sharply increasing incidence of "sporadic" cancers that occurs with advancing age. In contrast, the pattern characterized by the AR CAG polymorphism is of a moderate gradient of risk across CAG lengths. Because this polymorphism influences the progression of "sporadic" cancers, the population attributable risk is quite high. For example, it is estimated that 59% of distant metastatic prostate cancer among men over 60 years is attributable to CAG lengths less than 24, the cut-off between the upper and middle tertile. Thus, this polymorphism may play a role in the majority of deaths due to prostate cancer.

The results provide strong evidence that the variability in the transactivity of the AR determines the risk of developing "aggressive" prostate cancer. These data may represent the first known germline polymorphism related to tumor promotion or progression in "sporadic" tumors. Moreover, these findings may help explain the higher rate of prostate cancer mortality among black men, and the tendency for blacks to be diagnosed with more extensive disease.

TA POLYMORPHISM IN PROSTATE CANCER

Methods

The participants in the Physician's Health Study, as described above, were used in this example as well.

Whole blood samples from cases and matched controls were received from the Physicians Health Study coded with the laboratory investigators blinded to the name and status of each sample. Genomic DNA was obtained from 500 μl of the thawed whole blood using a commercially available kit (QIAamp DNA extraction kit, QIAGEN, Chatsworth, Calif., USA). DNA concentration and purity were determined by UV absorbency on a Beckman DU640 spectrophotometer. Each sample was diluted to a final concentration of 20 ng/μl and stored at −20° C. until needed. No storage time exceeded 6 months.

Twenty to 40 nanograms of sample DNA was added to the PCR reaction mixture which included primers (previously described by Davis, D. L. and Russell D. W., Ham. Mal. Genet. 6 (2):820 (1993) (6)) 5'-GCTGATGAAAACTGTC AAGCTGCTGA-3' (SEQ ID NO:3) and 5'-GCCAGCTGGCAGAACGCCAGGAGAC-3' (SEQ ID NO:4) at a concentration of 1.0 μM each along with 50 mM KCl, 1.5 mM MgCl2, 125 μM each dNTP, and 1.5 units of AmpliTaq® (Perkin Elmer) in a final volume of 22 microliters. All amplifications were performed using MicroAmp® tubes (Perkin Elmer).

A Perkin Elmer GeneAmp PCR System 9600 thermocyler was programmed for two step PCR. After 2 minutes at 94° C., samples were initially cycled 31 times with a melting step at 88° C. for 15 seconds and an annealing and elongation step at 68° C. for 35 seconds. There was a final elongation step for 5 minutes at 68° C. These parameters result in exuberant amplification of the TA(0) and TA(9) alleles. However, after the initial round of amplification, no TA(18) alleles were clearly identified. One sample which did not amplify was subjected to different cycling parameters and eventually proved to be a patient homozygous for TA(18). Using this patient's DNA mixed with DNA from a patient homozygote for TA(0), the cycling parameters were optimized until a clear band for the TA(18) allele was reliably detected. All samples were then repeated with new parameters: 94° C. for 2 minutes followed by 30 cycles of 94° C. for 30 seconds then 64° C. for 1 minute, 30 seconds, and a final elongation for 8 minutes at 68° C. Each set of 33 samples was run in parallel with a positive control (TA(18) DNA mixed with TA(0) DNA in a 1:1 ratio) and a negative control (H20). Samples that had an ambiguous result or any set of 33 with a poor positive control were repeated.

Sensitivity experiments using DNA from known homozygotes for TA(0), TA(9), and TA(18) demonstrated the assay's ability to detect a 1:5 ratio of the different alleles. For example, clear signal of lengths consistent with TA(0) and TA(18) were visible when 3.3 nanograms of TA(18) were mixed with 16.7 ng of TA(0) DNA and amplified with the second cycling parameters listed above.

The PCR reaction clearly favored the shorter alleles, however, and the longer bands in heterozygotes were frequently fainter than the shorter bands. The initial cycling parameters favored the shorter TA(0) allele to such a degree that no TA(18) were identified. The final cycling parameters reliably amplified the positive control. If there was any ambiguity, samples were repeated. All samples, with the exception of the 4 samples with TA(18), were typed consistently in both rounds of amplification. DNA sequencing of one representative homozygote from a patient who was TA(0), TA(9) and TA(18) confirmed that the bands identified correlated with the expected genotype. Similarly, the heterozygotes which were sequenced also had the expected allele sequence.

After amplifications, 15 µl of amplified product was separated using a 2@ agarose gel and compared with HindIII digested PhiX DNA (New England Biolabs, Massachusetts, USA) after ethidium bromide staining. The TA allele families can visually be discerned as either TA(0), TA(9) or TA(18). A representative homozygote for each TA allele family was purified using QIAquick Spin PCR purification columns (QIAGEN, Germany) and the DNA sequence determined at the Dana Farber Core Facility. TA alleles from representative heterozygotes with the TA(9) and TA(18) allele family were isolated using a MERmaid kit (Bio 101, California, USA) and the DNA sequence was determined with the same methodology. Identification of 2–4 base pair differences is not possible with these separation methods and each allele was lumped into one of the TA families described previously. The genotype for each sample was recorded and statistical analysis was performed.

Genotype frequency by case control status, including that for aggressive cancers separately, was determined. Conditional logistic regression analyses using the SAS statistical software (SAS Institute Inc., N.C., USA) was used to compute odds ratios and 95% confidence intervals. To examine aggressive cases, unconditional logistic regression controlling for age and smoking, the matching variables wag used. This allowed utilization of information from controls matched to non-aggressive cases when analyzing the aggressive cases. Potential confounding by alcohol consumption, multivitamin use, body mass index and exercise level on the 1982 questionnaire and aspirin use based on randomization, was addressed by including these as covariants in multivariate models. All p-values are two sided.

Results

The allele frequency among controls was 0.844 (n=621) for TA(0), 0.152 (n=112) for TA(9), and 0.004 (n=3) for TA(18). The table below indicates the frequencies of the 5 genotypes that we observed in this population by case-control status in this population. No appreciable difference in case-control status for the prevalence for men heterozygous in the TA(9) allele was found, but an excess of controls was observed for men homozygous for TA(9) or TA(18).

TABLE 4

| Group | TA(0)/TA(0) | TA(0)/TA(9) TA(0)/TA(18) | TA(9)/TA(9) TA(18)/TA(18) |
|---|---|---|---|
| Total Prostate Cancer | 1.0 (reference) | 0.94 (0.68–1.30) | 0.32* (0.10–1.02) |
| Aggressive Prostate Cancer | 1.0 (reference) | 0.91 (0.60–1.38) | 0.16 (0.02–1.26) |

*P = 0.05

Next the relative risks for total and for aggressive prostate cancers according to genotype frequency was examined. Because of the rarity of the TA(18) allele in this population, men with TA(18) and the men with TA(9)were combined. A priori decision was based on the assumption that any functional effect of either TA(9) or TA(18) would likely be in a similar direction. It was found that men having the TA(0)/TA(9) or TA(0)/TA(18) genotype were not at appreciably lower or higher risk of total prostate cancer. However, homozygotes (TA(9)/TA(9) or TA(18)/TA(18)) were at appreciably lower risk (OR=0.23, CL 0.10–1.02). Although only 16 such men existed, this inverse association achieved conventionally statistical significance (p=0.05, two sided). Also of note, the upper bound confidence interval of 1.02 provides strong evidence against a higher risk of prostate cancer among homozygotes. When analyses was limited to aggressive prostate cancer, the inverse association with homozygotes became even stronger and a weak non-significant inverse association among the heterozygotes became evident (see Table 5).

TABLE 5

| Group | Controls (n = 368) | Cases (n = 368) | Aggressive cases (n = 182) |
|---|---|---|---|
| TA(0)/TA(0) | 0.72 (n = 265) | 0.745 (n = 274) | 0.758 (n = 138) |
| TA(0)/TA(9) | 0.245 (n = 90) | 0.237 (n = 88) | 0.231 (n = 42) |
| TA(0)/TA(18) | 0.0027 (n = 1) | 0.0054 (n = 2) | 0.0054 (n = 1) |
| TA(9)/TA(9) | 0.03 (n = 11) | 0.011 (n = 4) | 0.0054 (n = 1) |
| TA(18)/TA(18) | 0.0027 (n = 1) | 0.00 (n = 0) | 0.00 (n = 0) |

Among controls for whom we had hormone levels, we examined levels of testosterone (T), sex hormone binding globulin (SHBG), dihydrotestosterone (DHT), estradiol (E2), and 3-alpha androstanediol glucuronide which is an index of 5 alpha reductase activity. No appreciable difference in means among men based on their SRD5A2 genotype (see Table 6) was observed.

TABLE 6

| Hormone Levels | Genotype | |
|---|---|---|
| | TA(0)/TA(0) | Heterozygote |
| T | 4.71 (4.43–4.99) | 5.11 (4.53–5.69 |
| DHT | 0.392 (0.35–0.43) | 0.44 (0.37–0.51) |
| T/DHT ratio | 0.089 (0.080–0.098) | 0.090 (0.076–0.104) |
| 3a ADG | 6.62 (6.12–7.12) | 6.76 (5.83–7.69) |
| SHBD | 23.6 (20.8–25.2) | 28.5 (23.2–33.8)* |

Discussion

This study provides the first case-control study that directly examines the association between the TA dinucleotide repeat in the 3' untranslated region of 5 alpha reductase and risk of CaP. The results are contrary to earlier presumptions that longer TA alleles may lead to an increased risk of CaP based on the indirect evidence that they are more frequent in African-Americans.

It is clear that racial differences exist in distribution of the TA polymorphism lengths. Reichardt and colleagues, in the largest multiethnic population yet typed, suggested that the TA(18) is exclusively in African-American men (Cancer Res. 55:3973–75 (1995)). In the Physicians Health Study, which is comprised of predominantly white men, there were 4 men with the TA(18). Although it is now shown that the allele is present among Caucasians, it is much less frequent than in African-Americans (<1% ($5_{1472}$) compared to 18% (17/94), respectively). The reason for this disparity and the clinical significance remains unknown.

The study revealed that in a mostly Caucasian population, being homozygous for the longer allele may in fact be protective from CaP. This result was just within conventional statistical significance with a p value of 0.05. Adding strength to the finding was the congruous finding that men with longer TA repeats had a trend towards less aggressive tumors as well. This analysis was underpowered because of low numbers.

The biological significance of this TA allele is unknown. Similar areas of TA-rich sequence in the 3' untranslated regions of other genes have been associated with messenger instability (Zubiaga, A. M., et al., *Mol. and Cellular Biol.*, 15(4):2219–2230 (1995)). One hypothesis is that with increasing TA length there is more messenger instability and lower resultant levels of 5 alpha reductase activity. This effect will most likely be subtle and it seems entirely consistent that very little effect is seen with heterozygotes and only in the homozygote state does the longer TA repeat protect against CaP. A lifetime of lower activity of 5 alpha reductase and lower intra-prostatic levels of DHT may provide the connection between the TA allele and risk of CaP.

Employing the above described methods, morbidity and mortality risks can be assessed in males who have not or have been diagnosed with prostate cancer. Armed with these additional criteria for assessing likelihood of aggressive onset or mortality, a male identified as being of increased risk can be screened for prostate cancer more frequently and aggressively in order to identify disease onset at the earliest stage possible. Upon onset of disease, the aggressiveness of the treatment protocol can be defined based, at least in part, by assessment of these new risk factors.

EXAMPLE 2

The CAG Repeat Within the Androgen Receptor Gene and its Relationship to Prostate Cancer The relationship between the polymorphic CAG repeat length of the androgen receptor gene, which is inversely correlated with transcriptional activation by the androgen receptor, and prostate cancer was further examined. The design was a nested case-control study within prospective cohort. The subjects were participants in the Physician's Health Study. The main outcome measures were five hundred and eighty-seven newly diagnosed cases of prostate cancer detected between 1982 and 1995, and 588 controls.
Results An inverse association between androgen receptor gene CAG repeat length and risk of prostate cancer was observed. For an increment of six CAG repeats, equivalent to the difference between the median CAG length in the upper versus lower tertile of CAG repeats, the relative risk of prostate cancer was 0.78 (95 percent confidence interval, 0.62–0.99; p=0.04). In particular, CAG repeat length was inversely associated with cancers characterized by extraprostatic extension or distant metastases (stage C or D) or high histologic grade (RR=0.61 (95 percent confidence interval, 0.45–0.82; p=0.001). The relative risk for an increment of six CAG repeats was 0.41 (95 percent confidence interval, 0.22–0.76; p=0.004) for distant metastatic prostate cancer and 0.48 (95 percent confidence interval, 0.25–0.95; p=0.04) for fatal prostate cancer. Variability in the CAG repeat length was not associated with low grade or low stage disease. Among cases, an inverse correlation between CAG repeat length and disease progression as indicated by stage and grade (p=0.001) was observed.
Conclusions The results demonstrate that shorter androgen receptor CAG repeat lengths predict higher grade and advanced stage of prostate cancer at diagnosis, and metastasis and mortality from the disease.

Cell division in the prostate gland is controlled by testosterone (Coffey D. S., *UICC Technical Report Series*, 48:4–23, Geneva: International Union Against Cancer, (1979). In the prostate cell, testosterone is converted to dihydrotestosterone (DHT) (Thigpen, A. E., et al., *N.E. J. Med.*, 327:1216–19 (1992)) which binds to the androgen receptor (AR) in the cell nucleus, and the DHT-AR complex then interacts with specific DNA sequences, modulating target gene activity. Encoded in exon 1 of the AR gene are polymorphic CAG repeats, which range normally from about 8 to about 31 and average about 20 (Edwards A., et al. *Genomics* 12:241–53 (1992)). The CAG repeats encode for polyglutamine chains in the transcriptional activation region of the AR. In transfection assays, the length of these polyglutamine chains correlate inversely with transcriptional activation by the AR (Chamberlain, N. L., et al., *Nucleic Acids Res.*, 22:3181–6 (1994); Kazemi-Esfarjani P., et al., *Human Molecular Genetics*, 4:523–7 (1995)). This inverse relationship is linear and includes the normal range (Kazemi-Esfarjani P., et al., *Human Molecular Genetics*, 4:523–7 (1995)). Expansion to greater than 40 repeats which, through an unknown mechanism, causes X-linked spinal and bulbar muscular atrophy (Kennedy's disease), leads to clinical androgen insensitivity despite normal serum testosterone levels in men (LaSpada, A. R., et al., *Nature*, 352:77–9 (1991); Arbizu, T., et al., *J. Neurol. Sci.*, 59:371–82 (1983); Igarashi, S., et al., *Neurology*, 42:2300–2 (1992)).

Several observations suggest indirectly that variation in the AR polyglutamine length, by modulating androgen activity, influences prostate carcinogenesis. African Americans, who have generally shorter CAG repeat lengths in the AR (Coetzee, G. A., Ross, R. K., *J. Natl. Cancer Inst.*, 86:872–3 (1994)), have a higher incidence and mortality rate from prostate cancer. The AR is located on the X-chromosome, and consistent with an X-linked genetic component for prostate cancer is that history of the disease in a brother carries greater risk than paternal history (Woolf, C. M., *Cancer*, 13:739–44 (1960); Monroe, K. R., et al., *Nature Med.*, 1:827–9 (1995); Narod, S. A., et al., *Nature Med*, 1:99–101 (1995); Steinberg, et al., *Prostate*, 17:33–47 (1990); Hayes, R. B., et al., *Int. J. Cancer*, 60:361–4 (1995); Whittemore, A. S., et al., *Am. J. Epidemiol.*, 141:732–40 (1995)). Irvine and colleaguees has suggested that certain forms of the AR characterized by their CAG repeats may be associated with prostate cancer *Cancer Res.*, 55:1937–40 (1995)). These observations led us to directly assess whether polymorphism in CAG repeat length in the AR is related to prostate cancer development and progression in the Physician's Health Study.

Methods

Study population

The Physician's Health Study was a randomized double-blind, trial of aspirin and betacarotene among 22,071 U.S. male physicians, aged 40 to 84 years in 1982 (Steering Committee of the Physicians Health Study Res. Group, *N. E. J. Med.*, 321:129–35 (1989)). The cohort is predominantly white (over 95%). Men were excluded if they reported a prior history of myocardial infarction, stroke, transient ischemic attacks, unstable angina, cancer (except for non-melanoma skin cancer), current renal or liver disease, peptic ulcer or gout, contraindication to use of aspirin, or current use of aspirin, other platelet-active agents or vitamin A supplements.

Study participants completed two mailed questionnaires before randomization in 1982, and additional questionnaires at six months, 12 months, and annually thereafter. Before randomization, blood kits were sent to all participants with instructions to have their blood drawn into vacutainer tubes containing EDTA, to centrifuge them, and to return the specimens (by overnight pre-paid courier) in polypropylene cryopreservation vials. The kit included a cold pack to keep the specimens cool until receipt the following morning, when they were aliquoted and stored at—82° C. Specimens were received from 14,916 (68%) of the randomized physicians. The lack of blood samples for some study participants is unlikely to have introduced selection bias, since it is unlikely that physicians who did or did not provide a sample would differ in terms of the relationship of the AR CAG polymorphism to subsequent prostate cancer experience.

Selection of Cases and Controls

When a participant reported a diagnosis of cancer on the follow-up questionnaires, medical records, including pathology reports, that were reviewed by study physicians from the End Points Committee, were requested. By 1995, we confirmed 591 cases of prostate cancer among the 14,916 who had provided blood. For each case, one control who had provided blood, had not had a previous prostatectomy, and had not reported a diagnosis of prostate cancer at the time diagnosis was reported by the case was selected. Controls were also matched on smoking status and age within one year, except for several very elderly cases for whom age had to be matched within two years. After 13 years of follow-up, over 99% of the men were still reporting morbidity events, and vital status was ascertained for 100%.

Medical Record Review

A study physician, unaware of assay results, reviewed medical records for each case to determine stage of diagnosis, tumor grade, and Gleason score. Stage was recorded according to he modified Whitmore-Jewett classification scheme (Beahrs, O. H., et al., *Manual for Staging of Cancer*, 4th ed., Philadelphia: J. B. Lippincott (1992)). If multiple tissue samples were examined, the highest reported grade and Gleason score were recorded. Cases without pathological staging were classified as indeterminate stage unless there was clinical evidence of distant metastases. High grade/stage cases were defined as those diagnosed at stage C or D (extraprostatic) plus those diagnosed at stage A or B or indeterminate with either poor histologic differentiation or Gleason score 7 or greater. Cases with clinical stage A or B or no pathological staging, and moderate or better histologic grade were classified as low grade/stage.

Analysis for CAG Repeat Length in the Androgen Receptor

Since the AR gene is X-linked, only one copy of the gene exists in men. The CAG repeat region resides in the first exon of the gene. A system to rapidly analyze the CAG repeat sequence length in a large number of samples was established. Five hundred microliters of whole blood were thawed from cases an controls and DNA was extracted utilizing the Qiagen QIAamp Blood Kit. A set of oligonucleotide primers that flank the CAG repeat (5'TCCAGAATCTGTTCCAGAGCGTGC3') SEQ ID NO:1 and 5'GCTGTGAAGGTTGCTGTTCCTCAT3'SEQ ID NO:2 were contructed. The DNA was amplified using these primers by polymerase chain reaction (PCR) to produce fragments of the N-terminal domain of the AR. Primers were fluorescently labelled. The length of these fragments varied only by the number of CAG repeats. For rapid and accurate assessment of fragment length, the DNA fragments were run on a 6% denaturing polyacrylamide gel by automated fluorescence detection (Genescan Applied Biosystems) in the Dana Farber Cancer Institute Molecular Biology Core Facility. Using a series of sequenced PCR products of varying size, fluorescently labelled DNA markers were used to create a standard curve of peak arrival time that in turn was used to calculate the length of an unknown PCR product automatically. Resolution of 1 base pair using this system was confirmed with direct DNA sequencing. The assays were conducted by laboratory personnel blinded to case-control status. Multiple samples were run per lane because of fluorescence labelling. Split samples were used to ensure quality control. It was possible to amplify the DNA for 587 of the 591 cases and 588 of the 591 controls (>99%).

Data Analysis

Analyses to determine whether AR CAG repeat length was related to the development of prostate cancer were conducted. Unlike the infiltrative or aggressive type of prostate cancer, the frequency of the latent non-infiltrative type of cancer varies very little among populations (Yatani, R., et al., *Int. J. Cancer*, 29:611–66 (1982)), suggesting that factors that influence initiation may differ from those that influence progression of prostate cancer; hence, additional analyses of tumors with a more aggressive phenotype as determined by histology (tumor grade or Gleason score), tumor stage, and fatality were conducted. The relative risk (estimated by the odds ratio) of developing total, high-grade, advanced-stage, distant metastatic, and fatal prostate cancer was examined. Unconditional logistic regression was used, controlling for age and smoking, the matching variables, to compute odds ratios and 95 percent confidence intervals, after first conducting conditional logistic regression to confirm similar results. By using unconditional logistic regression, it was possible to utilize information from all controls in the analyses limited to a subset of cases (e.g., high grade or fatal cases).

In addition, analyses within the cases only, were conducted to examine various parameters of aggressive behavior (stage, grade, fatality) in relation to CAG repeat length. Because AR transcriptional activation function decreases linearly across the entire CAG spectrum (Chamberlain, N. L., et al., *Nucleic Acids Res.*, 22:3181–6 (1994); Kazemi-Esfarjani P., et al., *Human Molecular Genetics*, 4:523–7 (1995)) CAG repeats were analyzed as a continuous variable in logistic models. This approach assumes that each one-unit increment in CAG repeat length is related to a constant increase or decrease in the natural logarithm of the odds ratio. In addition, men were divided into categories of number of CAG repeats to observe if non-monotonic increases existed across levels (e.g., if a threshold effect existed). The categorization (ranging from $\leq 19$ to $\geq 26$ repeats) was based on approximating relatively equal numbers in the categories, although the numbers fluctuated somewhat because of the very uneven distribution of CAG repeats. Potential confounding by alcohol consumption, multivitamin use, body mass index, and exercise level on the 1982 questionnaire, and aspirin use based on randomization was addressed by including these as covariates in multivariate models. All p-values are two-sided.

Results

The number of CAG repeats in the AR ranged from 12 to 35 among cases and from 6 to 39 among controls. The mean (and standard deviation) for CAG repeats was 21.8 (3.1) for cases and 22.0 (3.3) for controls. The difference in means was not statistically significant (P=0.25). Among the controls, the mode of the distribution occurred at 21 CAG repeats (17% of men), approximately 10% of the men fell in each-of 22, 23, 24, and 26 repeats, and a sharp drop-off occurred at 27 CAG repeats.

Next the relative risks (estimated by odds ratios) for total and sub-groups of prostate cancers by CAG repeat length were examined. For total prostate cancer, an inverse association between CAG repeat size and risk of disease (P=0.04) (Table 7) was observed.

TABLE 7

Odds ratio (OR) of prostate cancer by length of CAG repeat length of the androgen receptor gene among men in the Physicians' Health Study (1982–1995)

| | CAG Length | | | | | | P-value |
|---|---|---|---|---|---|---|---|
| | ≤19 | 20 | 21 | 22–23 | 24–25 | ≥26 | (trend) |
| Controls | 116 | 65 | 101 | 119 | 115 | 72 | |
| Total Prostate Cancer (n) | 131 | 69 | 113 | 116 | 98 | 60 | |
| OR* | 1.0 | 0.94 | 0.99 | 0.86 | 0.75 | 0.73 | 0.04 |
| 95% CI | — | (0.62–1.44) | (0.68–1.44) | (0.60–1.23) | (0.52–1.09) | (0.48–1.13) | |
| High grade/stage Prostate Cancer (n)** | 68 | 38 | 55 | 47 | 37 | 24 | |
| OR* | 1.0 | 1.00 | 0.92 | 0.67 | 0.55 | 0.56 | 0.001 |
| 95% CI | — | (0.60–1.66) | (0.59–1.45) | (0.43–1.06) | (0.34–0.90) | (0.32–0.98) | |
| Low grade/stage Prostate Cancer (n) | 59 | 30 | 58 | 69 | 58 | 35 | |
| OR* | 1.0 | 0.90 | 1.13 | 1.15 | 0.98 | 0.96 | 0.86 |
| 95% CI | — | (0.52–1.55) | (0.72–1.78) | (0.74–1.77) | (0.63–1.54) | (0.57–1.60) | |
| Fatal Prostate Cancer (n) | 14 | 6 | 9 | 4 | 7 | 3 | |
| OR* | 1.0 | 0.77 | 0.68 | 0.28 | 0.48 | 0.33 | 0.04 |
| 95% CI | — | (0.28–2.14) | (0.28–1.68) | (0.09–0.89) | (0.18–1.24) | (0.09–1.21) | |
| Metastatic (Distant) Prostate Cancer (n) | 17 | 11 | 9 | 9 | 7 | 3 | |
| OR* | 1.0 | 1.12 | 0.56 | 0.53 | 0.38 | 0.27 | 0.004 |
| 95% CI | — | (0.49–2.58) | (0.23–1.32) | (0.23–1.25) | (0.15–0.97) | (0.07–0.96) | |

*Odds ratio (OR) and 95 percent confidence interval (95% CI) for various categories of CAG repeats relative to men with repeat size ≤19. OR controlled for age (in 5-year age categories) and smoking (past, current) by nonconditional logistic regression.
**Tumors with Gleason grade ≥7 or high grade, or those with extension outside the prostate gland (stage C or D).

Statistically significant inverse associations for cancers characterized by various indicators of high grade or advanced disease were noted, whereas no association was noted for low grade or low stage cancer. A strong and statistically significant (P=0.04) inverse association between CAG repeat length and fatal prostate cancer was observed. AR CAG length was not correlated with any cofactor considered (age, year of diagnosis, alcohol intake, physical activity, multivitamin use, body mass index, and aspirin use); hence, the results were unaltered when these were included as covariates in models. Table 8 shows the odds for a six-CAG increment (equivalent to the difference between the median CAG repeat between the high and low tertiles). Also shown are results for high grade and advanced stage lesions separately.

TABLE 8

Odds ratio of prostate cancer for a CAG microsatellite repeat length increment of 6 in the androgen receptor gene among men in the Physicians' Health Study

| Prostate Cancer | Cases | Odds Ratio* (6 increment in CAG) | 95% Confidence Interval | P-value |
|---|---|---|---|---|
| Total | 587 | 0.78 | (0.62–0.99) | 0.04 |
| High grade/stage** | 269 | 0.61 | (0.45–0.82) | 0.001 |
| Low grade/stage | 309 | 0.98 | (0.73–1.30) | 0.86 |
| High grade | 210 | 0.63 | (0.45–0.88) | 0.007 |
| Advanced stage | 180 | 0.57 | (0.40–0.81) | 0.002 |
| Metastatic (Distant) | 56 | 0.41 | (0.22–0.76) | 0.004 |
| Fatal | 43 | 0.48 | (0.25–0.95) | 0.04 |

*Odds ratio is calculated by modeling CAG as a continuous variable in an unconditional logistic model and computing the odds ratio for a six CAG increment (increment from median of low to median of high tertile of CAG repeat length).
**Includes tumors with Gleason grade ≥7 or high grade or advanced stage (C or D).

Initially observed these relationships were observed in 367 cases mostly diagnosed by 1991 before he widespread use of prostatic-specific antigen (PSA) for screening. Subsequently this association was confirmed in 220 new cases diagnosed after March 1992, during the era of prevalent use of PSA for screening. The combined 587 cases comprise the cases described in this report. The relative risks were very similar in the initial analysis (for high stage/grade lesions, RR (for a CAG increment of 6)=0.66 (95 percent confidence interval=0.45–0.96; P=0.03), and RR=0.52 (95 percent confidence interval=0.29–0.91; P=0.02), for cases during the subsequent time period. No appreciable association was observed for low grade/stage cancers during either time period.

Next the relation between AR CAG repeat length in the cases alone, assessing the different classes of tumors (Table 9) was examined.

TABLE 9

Mean CAG length in the androgen receptor gene (± standard error of the mean)

| | n | Mean CAG (±SEM) | P-value |
|---|---|---|---|
| Low grade/stage Prostate Cancer | 309 | 22.18 (±0.19) | * |
| High grade/stage Prostate Cancer | 269 | 21.36 (±0.18) | 0.002 |

TABLE 9-continued

Mean CAG length in the androgen receptor gene
(± standard error of the mean)

|  | n | Mean CAG (±SEM) | P-value |
| --- | --- | --- | --- |
| Advanced Prostate Cancer | 180 | 21.36 (±0.22) | 0.005 |
| High-grade Prostate Cancer | 210 | 21.42 (±0.20) | 0.007 |
| Metastatic Prostate Cancer | 56 | 20.89 (±0.38) | 0.006 |
| Fatal Prostate Cancer | 43 | 21.05 (±0.46) | 0.03 |

*P-value based on t-test for difference versus mean androgen receptor gene CAG length among low grade/stage prostate cancer cases.

Men with low grade/stage tumors had a slightly higher CAG repeat length than controls (22.18 versus 22.00), but this difference was not statistically significant. Case defined by high grade or stage had lower mean CAG repeat length than low grade/stage cases. These differences were statistically significant for advanced cases (P=0.005) and high grade cases (P=0.002), and for distant metastatic or fatal cases (P=0.006), and for fatal cases (P=0.04). A test for trend in CAG repeat length across 3 levels of disease (non-aggressive disease, high grade or regional disease (beyond the prostatic capsule), and distant metastases) using progressive ordinal values in a linear regression model was statistically significant (P=0.001). At the extreme range of CAG repeats, the relationship between repeat length and aggressive phenotype was particularly strong. Comparing men with repeat lengths $\leq 15$ to those $\geq 30$, the odds ratio for high grade/stage versus low grade/stage prostate cancer was 30; although only 24 men fell in this range (4% of the total), this result was statistically significant (P=0.006).

Tumors with high grade are more likely to be of advanced stage, but even after excluding those with both high grade and advanced stage, shorter CAG repeats were observed independently for high grade (P=0.03) and advanced stage (P=0.02) cases only. Thus, CAG repeat length was independently related to both tumor grade and stage at diagnosis.

Discussion

Cell division in the prostate gland is mediated through androgens. Various lines of evidence suggest that the occurrence and progression of malignancies of this gland are influenced by androgen stimulation. Prostate cancer is sensitive to androgens and often regresses when androgen stimulation is withdrawn (Coffey D. S., *UICC Technical Report Series*, 48:4–23, Geneva: International Union Against Cancer, (1979). Malignancies of the prostate occur rarely in castrated men (Hovenian, M. S. and Deming, C. L., *Surg. Gynecol. Obstet.*, 86:29–35 (1948)), and the prolonged administration of high levels of testosterone has induced prostate cancer in rats (Noble, R. L., *Cancer Res.*, 37:1929–33 (1977); Pollard, M., et al., *Prostate*, 4:563–8 (1982)). While abnormally low levels of androgens are associated with low risk of the disease and high levels induce cancer in animals, the question whether androgenicity within the normal range is associated with moderate differences in risk is unsettled.

The action of androgens is ultimately mediated through the androgen receptor (AR). In transfection experiments, longer AR polyglutamine repeat lengths encoded by CAG repeats are associated with lower transcriptional activation function. Two laboratories (Chamberlain, N. L., et al., *Nucleic Acids Res.*, 22:3181–6 (1994); Kazemi-Esfarjani P., et al., *Human Molecular Genetics*, 4:523–7 (1995)) have independently established that this relationship is length-dependent, and occurs even within the normal range of CAG repeats. In contrast to binding of the AR to DNA, binding of androgens occurs in a different region of the AR which is unaffected by this polymorphism in polyglutamine length. Abnormally high CAG repeat length ($\geq 40$), which through an unknown mechanism causes spinobulbar muscular atrophy or Kennedy syndrome, is associated with clinically overt androgen insensitivity in men (LaSpada, A. R., et al., *Nature*, 352:77–9 (1991); Igarashi, S., et al., *Neurology*, 42:2300–2 (1992)). Based on a small sample (n=16), women with normal testosterone levels but with idiopathic hirsutism exhibited an inverse correlation between degree of hirsutism and CAG repeat size within the normal range (r=0.60, P=0.01) (Legro, R. S., et al., *obstet. Gynecol*, 83:701–6 (1994)).

Given clear evidence of clinical androgen insensitivity with long CAG repeat lengths and the linear gradient between CAG repeat length and AR transcriptional activation in vitro, a reasonable supposition is that variation within the normal range is associated with differences in transcriptional activation, albeit modest, in vivo. Based on the assumption that androgens are critical to prostate cancer development or progression, Coetzee and Ross (Coetzee, G. A., Ross, R. K., *J. Natl. Cancer Inst.*, 86:872–3 (1994)) had hypothesized that variation in transactivational activity by the AR, related to polymorphic CAG repeats, influences prostate carcinogenesis. Also of potential relevance, a somatic mutation resulting in a contraction of the CAG microsatellite ($CAG_{24-18}$) was observed in an adenocarcinoma of the prostate (Schoenberg, M. P., et al., *Biochem. Biophys. Res. Comm.*, 198:74–80 (1994)), although whether this contraction was involved in the development or progression of the tumor or is an epiphenomenon is unknown.

The hypothesis that polymorphism in the CAG repeat which influences transcriptional activation function of the AR is related to prostate cancer development was examined. This hypothesis was tested in a large, prospective study, and it was found that variability in the CAG repeats of the AR was associated with prostate cancer and was particularly closely related to an aggressive phenotype, as defined by high histological grade, extension through the prostate gland, presence of distant metastasis at diagnosis, and mortality from the disease. A highly significant association occurred independently for both tumor grade and stage, increased in magnitude with degree of aggressive behavior, such as distant metastases and mortality, and occurred consistently over time in this cohort, arguing strongly that this was not a chance finding. Based on the study by Kazemi-Esfarjani and colleagues (Hum. Mol. Genet. 4:523–7 (1995)), it was estimated that each additional polyglutamine repeat would produce approximately a 2 percent decrease in transcriptional activation function by the Ar. Thus, a 12 percent differential in transcriptional activation is predicted for an increment of 6 CAG repeats. Although the magnitude of the effect of the AR polyglutamine length and transcriptional activation function in vitro might appear relatively modest, these differences over a lifetime might have a substantial impact. Using a mathematical model which assumes that prostate cancer risk is directly proportional to cumulative mitotic activity, Ross et al. have estimated that a 13% difference in testosterone-stimulated mitotic activity would result in a 2.8-fold difference in prostate cancer incidence (Ross, R. K., *Accomplishments in Cancer Research*, 219–28, (1992)). For a decrement of 6 CAG repeats or about 12% difference in transcriptional activation, the data herein predict a RR of 2.4 for metastatic disease and 2.0 for fatal disease, which are well within the magnitude as predicted by the model. These results also suggest that androgen stimulation within normal limits is a critical determinant of prostate cancer risk.

Most known germline mutations that confer higher risk of cancer (e.g. BRCA1 in breast, mismatch pair genes in colon, putative prostate cancer suppressor gene) are characterized by early age of disease onset, high population attributable at young ages, but a relatively low population attributable risk due to the sharply increasing incidence of "sporadic" cancers that occurs with advancing age. In contrast, the pattern characterized by the AR CAG polymorphism is that a moderate gradient of risk occurs across the spectrum of CAG repeats. Because this polymorphism influences the progression of "sporadic" cancers, the population attributable risk may be quite high. For example, it is estimated herein that among men in the lowest tertile of CAG repeat length, over half of the metastatic cancers are attributable to the relatively short CAG repeat length.

African-American men have on average higher PSA values, about a two-fold higher rate of metastatic prostate disease and mortality, and larger tumor volumes, even when they have equal access to health care as whites (Brawn, P. N., et al., *Cancer*, 71:2569–73 (1993); Moul, J. W., et al., *JAMA*, 274:1277–81 (1995)). Although the similar access to care does not assure equivalent utilization, these data are strongly indicative of a more aggressive tumor biology among blacks. Black men tend to have on average considerably shorter AR CAG repeats than white men in the U.S.; for example, about 7% of white men have repeat lengths less than 19 as compared to 40% of black men (Edwards A., et al. *Genomics* 12:241–53 (1992)). U.S. black men also have higher levels of bioavailable testosterone than whites (Ross, R. K., et al., *J. Natl. Cancer Inst.*, 76:45–8 (1986)) and appear exposed to higher levels of estrogen and testosterone in utero (Henderson, B. E., et al., Br. J. Cancer, 57:216–18 (1988)). Both hormonal levels and the AR responsitivity may contribute to higher rates of prostate cancer mortality among African-Americans.

The results herein provide strong evidence that the variability in the transcriptional activation function of the AR is associated with the risk of developing prostate cancer and in particular aggressive prostate cancer. These data represents the first known germline polymorphism related to tumor promotion or progression in "sporadic" tumors. Moreover, these findings help explain the higher rate of prostate cancer mortality among black men, the tendency for blacks to be diagnosed with more extensive disease, and the apparent X-linked component to prostate cancer risk. Our results are consistent with a substantial effect of CAG repeat length. Polymorphisms in the AR CAG-lengths has implications regarding prevention, screening, and treatment for prostate cancer.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A method for prognosis of prostate cancer in a male comprising: (a) determining the length of the CAG trinucleotide repeat of exon 1 of the androgen receptor gene and/or the length of the TA dinucleotide repeat of the 5 alpha reductase Type II gene obtained from DNA of the male and (b) correlating the length of the repeat with the aggressiveness and mortality risk of the cancer in the male.

2. The method of claim 1 wherein the DNA is genomic DNA.

3. The method of claim 2 wherein the DNA is obtained from non-cancerous cells.

4. The method of claim 3 wherein the DNA is obtained from a tissue or blood sample.

5. The method of claim 4 wherein the length of the repeat is determined by PCR.

6. The method of claim 4 wherein the aggressiveness and mortality risk of the cancer occurs at the age of at least about 60 years in the male.

7. The method of claim 6 wherein the male is at least about 60 years of age.

8. The method of claim 6 wherein the male is less than about 60 years of age.

9. A method for prognosis of prostate cancer in a male comprising:

(a) obtaining DNA from the male wherein the DNA comprises the CAG trinucleotide repeat of exon 1 of the androgen receptor gene and/or the length of the TA dinucleotide repeat of the 5 alpha reductase Type II gene or its complement; and (b) determining length of the repeat; and (c) comparing the length of the repeat with the length of the repeat in a male population individuals;
wherein the length of the repeat is prognostic of the aggressiveness and mortality of the prostate cancer.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

TCCAGAATCT GTTCCAGAGC GTGC                                   24

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GCTGTGAAGG TTGCTGTTCC TCAT                                   24

(2) INFORMATION FOR SEQ ID NO:3:

(i) SEQUENCE CHARACTERISTICS:
      (A) LENGTH: 26 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

GCTGATGAAA ACTGTCAAGC TGCTGA                                              26

(2) INFORMATION FOR SEQ ID NO:4:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

GCCAGCTGGC AGAACGCCAG GAGAC                                               25
```